United States Patent [19]

Bokerman et al.

[11] Patent Number: 4,985,579

[45] Date of Patent: Jan. 15, 1991

[54] REMOVAL OF HYDROGEN-CONTAINING SILANES FROM ORGANOSILANE MIXTURES

[75] Inventors: Gary N. Bokerman, Madison, Ind.; James E. Hampton; John G. Uhlmann, both of Midland, Mich.

[73] Assignee: Dow Corning Corporation, Midland, Mich.

[21] Appl. No.: 478,720

[22] Filed: Feb. 8, 1990

Related U.S. Application Data

[63] Continuation of Ser. No. 422,191, Oct. 16, 1989, abandoned.

[51] Int. Cl.$^5$ ............................................... C07F 7/08
[52] U.S. Cl. ................................................... 556/466
[58] Field of Search ......................................... 556/466

[56] References Cited

U.S. PATENT DOCUMENTS 4,297,500 10/1981 Finke et al. .......................... 556/466
4,421,926 12/1983 Tolentino ...................... 556/466 UX

OTHER PUBLICATIONS

Sommer et al., J. Org. Chem. 32:2470, 1967.

*Primary Examiner*—Paul F. Shaver
*Attorney, Agent, or Firm*—William F. Boley

[57] ABSTRACT

The instant invention is a process for the removal of hydrogen-containing silane impurities from organosilanes with similar boiling points. In the instant invention, the hydrogen-containing silane is reacted with a hydrogen halide to replace the hydrogen on the silane with a halide and create a modified silane. The substitution of the heavier halide for the hydrogen, increases the boiling point of the modified silane. This increase in boiling point facilitates separation by distillation of the modified silane impurity from the desired organosilanes.

26 Claims, No Drawings

REMOVAL OF HYDROGEN-CONTAINING SILANES FROM ORGANOSILANE MIXTURES

This is a continuation of copending application Ser. No. 422,191 filed on Oct. 16, 1989, abandoned.

BACKGROUND OF THE INVENTION

This invention relates to a process for the conversion of hydrogen-containing silane impurities to non-hydrogen containing silanes to facilitate the isolation and removal of these impurities from the desired organosilane product.

High-purity difunctional organosilanes, particularly diorganodihalosilanes, are needed for the preparation of organopolysiloxanes utilized in the manufacture of silicones. For example, the preparation of high-quality, high-performance silicone elastomers require that the difunctional organosilane contain a minimum level of trifunctional and tetrafunctional materials, to levels of a few parts per million on a molar basis.

Hydrogen-containing silane materials are a potential source of additional functionality. The hydrogen atom on a silane molecule is susceptible to cleavage, especially under the basic conditions employed during the production of siloxane materials. For the purposes of the instant invention, the term "functionality" is used to describe the ability of silane species to form a linear structure (difunctionality) a branched structure (trifunctionality) or a network structure (tetrafunctionality).

In the preparation of high-performance silicone elastomers, difunctional silane monomers with a minimum of trifunctional and tetrafunctional materials is a necessity. For example, $(CH_3)_2SiCl_2$ with $(C_2H_5)HSiCl_2$ impurity would result in a dimethyl siloxane polymer with hydrogen-containing siloxane units. Cleavage of the H atom would result in a branch (trifunctionality) on the siloxane chain. Such a branch can reduce the desired physical characteristics of the silicone elastomer subsequently formed from the polymer.

Organosilanes are typically manufactured by a direct process of reacting an organic halide with silicon in the presence of a catalyst. The resultant mixture is conventionally separated into the individual species by distillation. In many instances, the boiling points of individual organosilane components are very close, creating a very difficult distillation operation. An example of such a combination is the mixture of dimethyldichlorosilane, $(CH_3)_2SiCl_2$, and ethyldichlorosilane, $(C_2H_5)HSiCl_2$. The boiling points of dimethyldichlorosilane and ethyldichlorosilane are approximately 4° C. apart. Reducing the ethyldichlorosilane content of dimethyldichlorosilane would require a distillation column of more than one hundred theoretical distillation trays and reflux ratios in the range of 100:1.

Sommer et al., J. Org. Chem. 32:2470–2472 (1967), discloses that organosilicon hydrides react with hydrogen halides in the presence of Group VIII metals to form organosilicon halides and hydrogen. Sommer studied the reaction of $(C_2H_5)_3SiH$ with HCl to produce $(C_2H_5)_3SiCl$. Sommer does not disclose or suggest the use of this reaction in a process for the purification of organohalosilanes.

Tolentino, U.S. Pat. No. 4,421,926, issued Dec. 20, 1983, discloses the co-alkoxylation of halosilanes to facilitate separation of close-boiling halosilane materials difficult to separate by conventional distillation. Tolentino discloses that all halosilanes will be converted to alkoxysilanes. Nowhere does Tolentino demonstrate or suggest the reaction of hydrogen-containing silanes. Tolentino neither discloses or suggests the preferential reaction of hydrogen-containing silanes, with no concurrent reaction of the non-hydrogen containing halosilane, to facilitate isolation and recovery of the desired organohalosilane.

SUMMARY OF THE INVENTION

The instant invention is a process for the purification of organosilanes from mixtures such as result from the direct process for the production of organosilanes. In the instant invention, hydrogen-containing silanes present as impurities in the organosilane mixture are converted to non-hydrogen-containing silane materials to facilitate their separation from the organosilane mixture. The organosilane mixture can then be separated by known methods, for example, distillation, to yield organosilanes reduced in hydrogen-containing silanes. It is a further objective of the instant invention to convert the hydrogen-containing silanes while not changing the desired organosilane products.

DESCRIPTION OF THE INVENTION

The instant invention is a process to minimize the level of hydrogen-containing silane in an organosilane isolated from an organosilane mixture. What is described is a process for purification of an organosilane mixture by reducing the hydrogen-containing silane content of the mixture, where the organosilane contains organic substituents selected from a group consisting of alkyl radicals of 1 to 6 carbon units and phenyl and where the hydrogen-containing silane has a boiling point close to the organosilane.

The process comprises contacting an organosilane mixture, a hydrogen halide, and a catalyst. The organosilane mixture comprises as a major portion the organosilane and as a minor portion the hydrogen-containing silane. The hydrogen-containing silane, present in the organosilane mixture, is reacted with the hydrogen halide in the presence of the catalyst to form a more halogenated silane. This results in a higher molecular weight silane with a higher boiling point, thus, facilitating separation by distillation. An organosilane having a reduced content of hydrogen-containing silane is isolated and recovered from the organosilane mixture.

The organosilane mixture to be purified will consist initially of at least an organosilane and a hydrogen-containing silane present as an impurity. Multiple organosilane species and multiple hydrogen containing silane species may be present in the mixture. Other materials may also be present.

The described process facilitates the separation of hydrogen-containing silane impurities from an organosilane mixture when the boiling point of the impurities and organosilanes are so similar that separation by standard methods is difficult. For the purpose of this invention, materials are similar in boiling point if the substitution of a halogen for a hydrogen on the hydrogen-containing silane can facilitate separation of the materials by distillation. For example, ethyldichlorosilane has a molecular weight of 129.1 and a boiling point of 74°–76° C. Separation of this impurity from dimethyldichlorosilane, molecular weight 129.0, boiling point 70°–71° C., is difficult by standard distillation means. The conversion of ethyldichlorosilane to ethyltrichlorosilane, molecular weight 163.5, boiling point 100°–101° C., can facilitate a distillation process for effecting separation and purification of the desired dimethyldichlorosilane. Preferred mixtures for the purpose of this invention are those containing a hydrogen-containing silane that has a boiling point within about 10° C. of an organosilane and said hydrogen-containing silane's boiling point can be increased by at least about 5° C. by substitution of a halogen for the substituent hydrogen.

Examples of the organosilanes that can be purified are methyltrichlorosilane, methyltrifluorosilane, ethyltribromosilane, n-propyltrichlorosilane, dimethyldibromosilane, trimethylchlorosilane, methyldiethylbromosilane, methyldi(t-butyl)chlorosilane, tetramethylsilane, tetraethylsilane, phenyltrichlorosilane, diphenyldichlorosilane, phenylmethyldichlorosilane, and diphenyldifluorosilane.

The hydrogen-containing silane impurity in the organosilane mixture can be, for example, silane, chlorosilane, bromosilane, fluorosilane, methylsilane, ethylsilane, dichlorosilane, dibromosilane, methylohlorosilane, ethylbromosilane, trichlorosilane, methyldichlorosilane, ethyldichlorosilane, dimethylchlorosilane, methyl(t-butyl)chlorosilane, or biphenyldichlorosilane.

The hydrogen-containing silane can be present in the organosilane mixture at a concentration in a range from about 10 parts per million (ppm) to 10 percent on a weight basis. The inventors believe that organosilane mixtures containing less than about 10 ppm hydrogen-containing silanes can be treated using the instant invention. However, efficiency of conversion may be reduced.

The hydrogen halide can be, for example, hydrogen fluoride, hydrogen bromide, or hydrogen chloride. Preferred is hydrogen chloride. The hydrogen halide should be present in excess of the stoichiometric amount required to react with the hydrogen-containing silane to effect maximum conversion of the hydrogen-containing silane to a halosilane.

The halosilane formed by the reaction of a hydrogen-containing silane and the hydrogen halide can be, for example, tetrafluorosilane, tetrachlorosilane, tetrabromosilane, methyltrichlorosilane, methyltribromosilane, ethyltrichlorosilane, ethyltribromosilane, dimethyldichlorosilane, methyl(tbutyl)dichlorosilane, or biphenyltrichlorosilane.

The catalyst is selected from a group of metals consisting of palladium, platinum, rhodium, ruthenium, nickel, osmium, iridium and compounds thereof. Preferred metals are palladium, platinum, ruthenium, rhodium, and nickel. The term "compounds thereof" includes inorganic compounds, for example, metal salts and oxides, as well as organometallic compounds.

The metal or metal compound can be supported on a solid substrate. The solid substrate can be any inert material of appropriate size and proper affinity for the metal or metal compound, for example, particulate carbon or silica. The preferred substrate is carbon. More preferred is carbon with a surface area of about 1000 $M^2/g$. It is preferred that the metals or their compounds be present on the solid substrate at a concentration from about 0.2 to 3 weight percent. The inventors believe that metal or metal compound concentrations lower than about 0.2 weight percent may facilitate the reaction of the hydrogen-containing silane with the hydrogen halide; however, With reduced efficiency as evidenced by lower conversions and longer residence times. Conversely, metals or metal compounds at concentrations greater than about 5 weight percent of the support material may be utilized; however, no significant benefit is perceived except in the case of nickel. A useful concentration range for nickel and nickel compounds is about 5 to 15 weight percent of the support material. A preferred concentration of nickel and nickel compounds is about 10 weight percent.

Unsupported metals and metal compounds, as described supra, can also function as equivalent catalysts in the described process. The unsupported catalyst can be soluble or a finely divided particulate in the organosilane mixture. A useful concentration range for the unsupported catalyst is about 500 to 10,000 ppm. Although higher concentrations of catalyst will work in the process, there is no perceived advantage. Concentrations lower than about 500 ppm of catalyst may work, but with a slower conversion rate. Contacting of the organosilane mixture, the hydrogen halide, and the catalyst can be effected in either the liquid or vapor phase. When a supported catalyst is used, it is preferred that contact and reaction occur in the vapor phase. In general, the contact and reaction temperature should be in the range of 30° C. to 150° C. It is preferred that the contact and reaction occur at a temperature which is greater than the boiling point of the organosilane mixture. As an example, the dimethyldichlorosilane mixture from the direct process should be treated at a temperature of about 70° C. to 100° C., with a contact time of 5 to 10 minutes. When using an unsupported catalyst, it is often desirable to run the reaction at a higher temperature than that required for a similar supported catalyst. A preferred temperature range for unsupported catalysts is about 100° C. to 200° C.

The reaction of hydrogen-containing silanes with a hydrogen halide in the presence of the catalyst is very rapid. Depending upon the concentration of the hydrogen-containing silane in the organosilane mixture, the reaction can occur within seconds or minutes. Where the hydrogen-containing silane is at concentrations of about 10 ppm to about 10 percent by weight of the mixture, a contact time with the catalyst greater than about one minute is preferred. More preferred, the contact time should be about five minutes to 30 minutes. Shorter residence times can be utilized, but depending upon the concentration of hydrogen-containing silane in the organosilane mixture, lesser conversion of the hydrogen-containing silane may occur. Longer residence times are perceived to have no further benefits.

Contacting the organosilane mixture containing as a minor portion the hydrogen-containing silane, with the catalyst, can be carried out in known configurations for contact of liquids or vapors with a catalyst. Examples of such configurations are packed columns, fluid bed reactors, and stirred tank reactors in which the catalyst is mixed with a liquid. A packed column of supported catalyst through which the organosilane mixture and hydrogen halide pass is a preferred configuration. In the case of a vapor phase reaction, means must be provided for vaporizing the organosilane mixture be fore it is passed through the catalyst. Means for vaporization can include, for example, such known operations as a tank-type vaporizer, a shell-and-tube heat exchanger, and the like.

The organosilane mixture is fed as a liquid by conventional means such as pumping. Hydrogen halide is fed as a gas by conventional means of feeding and controlling gases.

Once the hydrogen-containing silanes in the organosilane mixture have been converted to organohalosilanes by reaction with a hydrogen halide, the isolation and recovery of the desired organosilane with reduced hydrogen-containing silane content can be effected. Isolation and recovery of the desired organosilane can be effected by conventional distillation.

The process as described can also be used to purify tetrachlorosilane from a silane mixture containing a hydrogen-containing silane. The silane mixture can contain, for example, organosilanes, organohalosilanes, tetrachlorosilane, and hydrogen-containing silanes. Tetrachlorosilane is present in the silane mixture as a major portion in relation to the hydrogen-containing silanes from which separation is desired.

So that those skilled in the art may better understand and appreciate the instant invention, the following examples are presented. These examples are presented to be illustrative and are not to be construed as limiting the claims as delineated herein.

EXAMPLE 1

Apparatus and procedures were established to evaluate the reaction of a hydrogen-containing silane impurity, contained in an organosilane mixture, with hydrogen chloride in the presence of a supported metal catalyst.

The reactor was a tube 22 mm in diameter and 26 cm long containing a support plate on which was placed the supported catalyst. The reactor was fitted with an electrical heater. Two ports were provided at the top of the reactor, one for an organosilane mixture feed and one for a hydrogen halide feed. A crude alkylsilane mixture was fed into the top of the reactor as a liquid. A zone in the reactor tube above the catalyst served as a preheater. The reactor tube effluent was condensed, sampled, and analyzed by gas chromatography.

The feed to the reactor tube was dimethyldichlorosilane (Me$_2$) which contained 133 ppm (by weight) ethyldichlorosilane (EtH). The catalyst was 0.2 weight percent palladium on carbon (Pd/C). The catalyst had a particle size of 4 to 8 mesh. The catalyst was dried 4 hours at 600° C. prior to use.

The Me$_2$/EtH mixture was fed to the reactor tube at a rate of 15 ml/h. The reaction tube was maintained at a showed 25 ppm EtH in Me$_2$. temperature of about 30° C. Analysis of the reactor effluent When the same procedure was conducted at 85° to 90° C., the Me$_2$ mixture contained less than 6 ppm EtH.

EXAMPLE 2

The same apparatus, procedures, and catalyst as used in Example 1 were used to evaluate the impact of feed rate on the conversion of the EtH in Me$_2$. The feed mixture was Me$_2$ which contained 4100 ppm EtH. Table 1 is a summary of the results of this evaluation. In Table 1, feed rate of the Me$_2$ mixture, expressed in ml/h, is designated as "Feed Rate"; EtH content of the reactor effluent, expressed in ppm, is designated as "ppm EtH."

TABLE 1

| Feed Rate | ppm EtH |
|---|---|
| 14.5 | <10 |
| 32.0 | 8 |
| 51.0 | 58 |
| 88.0 | 880 |

EXAMPLE 3

The reactor system was modified to change the direction of flow of the reactants in the reactor tube. A reactor tube 12 mm in inside diameter and about 50cm in length was charged with 30 cc of the 2% Pd/C catalyst previously described. The reactor tube was connected to the top of a 1000 ml flask with a surrounding heating mantle. The heated flask served as a preheater and vaporizer for a liquid alkylsilane feed. Vapors passed from the flask up through the catalyst bed.

A feed mixture containing 4100 ppm EtH in Me$_2$ was fed to the heated flask at a rate of 88 ml/h. The effluent was condensed and analysis showed the Me$_2$ mixture contained less than 5 ppm EtH.

EXAMPLE 4

Several Group VIII metal materials supported on carbon were evaluated as a catalyst for the reaction of hydrogen-containing silicon materials with hydrogen chloride.

The apparatus and procedures were similar to those utilized in Example 3.

Five different metals on carbon and one metal salt on carbon were evaluated for catalytic activity. Also, for comparison, a sample of activated carbon similar to the support used for the metal materials was tested. The supported metal catalysts evaluated were as follows: palladium (Pd/C), platinum (Pt/C), rhodium (Rh/C), ruthenium (Ru/C), and nickel (Ni/C). The metal salt evaluated was palladium chloride (PdCl$_2$/C) on carbon. The Pd/C, PdCl$_2$/C, and Ni/C were purchased from Alpha Products Division, Morton-Thiokol. The Pt/C, Rh/C, and Ru/C, all with a surface area of about 1000 M$^2$/g, were purchased from Engelhard.

Temperature in the vaporizer/preheater flask ranged from about 185° to 200° C. The organosilane mixture was Me$_2$ containing about 330 to 440 ppm EtH. Residence times of the organosilane vapors in the catalyst bed were computed based upon the liquid organosilane feed rate and the volume of catalyst within the bed. The temperature of the vapors exiting the catalyst bed was also monitored.

Table 2 is a summary of the results of this evaluation. Table 2 reports the catalyst used, designated as "Catalyst"; the catalyst volume, in cc, designated as "Vol Cat"; the organosilane liquid feed rate, in cc/h, designated as "Feed"; residence time in minutes is designated as "Res T"; temperature of the vapors exiting the reactor, in degree centigrade, is designated as "Temp"; and percent conversion of the EtH to ethyltrichlorosilane is designated as "% Conv."

TABLE 2

| Catalyst | Vol Cat (cc) | Feed (cc/h) | Res T (Min.) | Temp (°C.) | % Conv |
|---|---|---|---|---|---|
| Carbon | 17 | 120 | 9 | 75 | 12 |
| 1% Pd/C | 20 | 60 | 20 | 70 | 100 |
| 1% Pt/C | 20 | 76 | 16 | 85 | 100 |
| 1% Rh/C | 20 | 70 | 17 | 90 | 100 |
| 1% Ru/C | 26 | 130 | 12 | 80 | 100 |
| 3% PdCl$_2$/C | 10 | 60 | 10 | 70 | 100 |
| 10% Ni/C | 11 | 62 | 11 | 70 | 77 |

EXAMPLE 5

Unsupported PdCl$_2$ was evaluated as a catalyst for the conversion of PhMeHSiCl as an impurity in PhMe$_2$SiCl. The phenylmethylchlorosilanes were mixed with the PdCl₂ catalyst in a reactor and the mixture was subjected to a flow of HCl gas injected below the liquid level. The flow rate was sufficiently high to keep the HCl bubbling through the liquid. The mixture was heated for specified periods of time and sample taken. The samples were analyzed by gas chromatography and gas chromatography/mass spectroscopy for product identification and quantification. The specific run conditions and results are presented in Table 3.

The temperature at which the reaction was run, in degrees centigrade, is designated as "Temp." The term "Run Time" refers to the time after initiation of the run at which a sample was taken for analysis. The column labelled "PdCl₂" lists the concentration of PdCl₂ employed in the run, in parts per million (ppm). The column labelled "PhMeHSiCl" lists the concentration of the hydrogen-containing silane impurity. The column labelled "% Conv." gives the percent reduction of PhMeHSiCl under the various reaction conditions.

TABLE 3

| Run No. | Temp. (°C.) | Run Time (Min.) | PdCl₂ (ppm) | PhMeHCl (ppm) | % Conv |
|---|---|---|---|---|---|
| 2 | 100 | 245 | 10,217 | 258 | 100 |
| 3 | 140 | 175 | 10,353 | 163 | 100 |
| 4 | 185 | 275 | 11,209 | 1155 | 100 |
| 5 | 185 | 10 | 0 | 540 | 34 |
| 6 | 185 | 10 | 10,799 | 247 | 100 |
| 7 | 190 | 10 | 1,189 | 6866 | 100 |

What is claimed is:

1. A process for purification of an organosilane mixture by reducing hydrogen-containing silane content of the organosilane mixture, where the organosilane mixture contains, as a major portion, organosilane species which contain at least one substituent selected from a group consisting of alkyl radicals of 1 to 6 carbon atoms and phenyl; and where the hydrogen-containing silane has a boiling point similar to that of at least one of the organosilane species;

the process comprising:

(A) contacting the organosilane mixture, a hydrogen halide, and a catalyst; where the organosilane mixture comprises as the major portion the organosilane species and as a minor portion the hydrogen-containing silane; where the catalyst is selected from a group consisting of nickel and nickel compounds, each supported on a solid substrate;

(B) reacting the hydrogen-containing silane in the organosilane mixture with the hydrogen halide, in the presence of the catalyst, to form an altered organosilane mixture containing a more halogenated silane.

(C) isolating and recovering the organosilane species from the altered organosilane mixture.

2. A process according to claim 1, where the catalyst is present on the solid substrate at a concentration of about 5 to about 15 weight percent of the solid substrate.

3. A process according to claim 1, where the solid substrate is carbon.

4. A process according to claim 3, where the carbon substrate has a surface area of about 1000 M²/g.

5. A process according to claim 1, where the hydrogen-containing silane has a boiling point within about 10° C. of the organosilane species, halogenation of the hydrogen-containing compound increases the boiling point of the hydrogen containing compound by at least 5° C., and isolating and recovering the organosilane species is effected by distillation.

6. A process according to claim 5, where the organosilane specie is dimethyldichlorosilane; the hydrogen-containing silane is ethyldichlorosilane; the halogen halide is hydrogen chloride; the ethyldichlorosilane is present in the organosilane mixture at a concentration less than about 10 weight percent based on total weight of the mixture; the hydrogen-containing silane is contacted with the hydrogen chloride in the presence of the catalyst at a temperature of about 70° C. to 100° C.; and the contact time is 5 to 10 minutes.

7. A process according to claim 1, where the organosilane specie is diphenyldichlorosilane and isolation and recovery is effected by distillation.

8. A process according to claim 1, where the organosilane specie is phenylmethyldichlorosilane and isolation and recovery is effected by distillation.

9. A process according to claim 1, where contacting the hydrogen-containing silane with the hydrogen halide in the presence of the catalyst is carried out in a vapor phase.

10. A process according to claim 1, where contacting the hydrogen-containing silane with the hydrogen halide in the presence of the catalyst is carried out in a liquid phase.

11. A process according to claim 1, where isolating and recovering the organosilane species with reduced content of hydrogen-containing silane is effected by distillation.

12. A process for purification of an organosilane mixture by reducing hydrogen-containing silane content of the organosilane mixture, where the organosilane mixture contains, as a major portion, organosilane species which contain at least one substituent selected from a group consisting of alkyl radicals of 1 to 6 carbon units and phenyl; and where the hydrogen-containing silane has a boiling point similar to that of at least one of the organosilane species;

the process comprising:

(A) contacting the organosilane mixture, a hydrogen halide, and an unsupported catalyst; where the organosilane mixture comprises as the major portion the organosilane species and as a minor portion the hydrogen-containing silane; where the catalyst is selected from a group of metals consisting of palladium, platinum, rhodium, ruthenium, nickel, osmium, iridium, and compounds thereof;

(B) reacting the hydrogen-containing silane in the organosilane mixture with the hydrogen halide, in the presence of the catalyst, to form an altered organosilane mixture containing a more halogenated silane, (C) isolating and recovering the organosilane species from the altered organosilane mixture.

13. A process according to claim 12, where the catalyst is selected from the group consisting of palladium, platinum, rhodium, and ruthenium.

14. A process according to claim 13, where the reacting of the hydrogen-containing silane in the organosilane mixture with the hydrogen halide in the presence of the catalyst, to form an altered organosilane mixture containing a more halogenated silane, is effected at a temperature of about 100° C. to 200° C.

15. A process according to claim 14, where the catalyst is a metal salt.

16. A process according to claim 15, where the metal salt is PdCl$_2$.

17. A process according to claim 14, where contacting the hydrogen-containing silane with the hydrogen halide in the presence of the catalyst is carried out in a liquid phase.

18. A process for purification of tetrachlorosilane from a silane mixture by reducing hydrogen-containing silane content of the silane mixture, where the silane mixture contains, as a major portion, tetrachlorosilane; and where the hydrogen-containing silane has a boiling point similar so that of tetrachlorosilane;

the process comprising:
(A) contacting the silane mixture, a hydrogen halide, and an unsupported catalyst; where the mixture comprises as the major portion tetrachlorosilane and as a minor portion the hydrogen-containing silane; where the catalyst is selected from a group of metals consisting of palladium, platinum, rhodium, ruthenium, nickel, osmium, iridium, and compounds thereof;
(B) reacting the hydrogen-containing silane in the silane mixture with the hydrogen halide, in the presence of the catalyst, to form an altered silane mixture containing a more halogenated silane;
(C) isolating and recovering the tetrachlorosilane from the altered silane mixture, the tetrachlorosilane having a reduced content of the hydrogen-containing silane.

19. A process according to claim 12, where the hydrogen-containing silane has a boiling point within about 10° C. of the organosilane species, halogenation of the hydrogen-containing silanes increases the boiling point of the hydrogen containing silane by at least 5° C., and isolating and recovering the organosilane species is effected by distillation.

20. A process according to claim 19, where the organosilane specie is dimethyldichlorosilane; the hydrogen-containing silane is ethyldichlorisilane; the halogen halide is hydrogen chloride; the ethyldichlorosilane is present in the organosilane mixture at a concentration less than about 10 weight percent based on total weight of the mixture; the hydrogen-containing silane is contacted with the hydrogen chloride in the presence of the catalyst at a temperature of about 100° C. to 200° C.; and the contact time is 5 to 10 minutes.

21. A process according to claim 12, where the organosilane specie is diphenyldichlorosilane and isolation and recovery is effected by distillation.

22. A process according to claim 12, where the organosilane specie is phenylmethyldichlorosilane and isolation and recovery is effected by distillation.

23. A process for purification of tetrachlorosilane from a silane mixture by reducing hydrogen-containing silane content of the silane mixture, where the silane mixture contains, as a major portion, tetrachlorosilane; and where the hydrogen-containing silane has a boiling point similar to that of tetrachlorosilane;

the process comprising:
(A) contacting the silane mixture, a hydrogen halide, and a catalyst; where the mixture comprises as the major portion tetrachlorosilane and as a minor portion the hydrogen-containing silane; where the catalyst is selected from a group consisting of nickel and nickel compounds, each supported on a solid substrate;
(B) reacting the hydrogen-containing silane in the silane mixture with the hydrogen halide, in the presence of the catalyst, to form an altered silane mixture containing a more halogenated silane;
(C) isolating and recovering the tetrachlorosilane from the altered silane mixture, the tetrachlorosilane having a reduced content of the hydrogen-containing silane.

24. A process according to claim 23, where the solid substrate is carbon.

25. A process according to claim 24, where the hydrogen-containing silane has a boiling point within about 10° C. of the tetrachlorosilane, halogenation of the hydrogen-containing silane increases the boiling point of the hydrogen-containing silane by at least 5° C., and isolating and recovering the tetrachlorosilane is effected by distillation.

26. A process according to claim 33, where the catalyst is present on the solid substrate at a concentration of about 5 to about 15 weight percent of the solid substrate.

* * * * *

UNITED STATES PATENT AND TRADEMARK OFFICE
CERTIFICATE OF CORRECTION

PATENT NO. : 4,985,579
DATED : January 15, 1991
INVENTOR(S) : Gary N. Bokerman; James E. Hampton; John G. Uhlmann It is certified that error appears in the above-identified patent and that said Letters Patent is hereby corrected as shown below:

On the title page:

Inventors: "Gary N. Bokerman, Madison, Ind.; James E. Hampton; John G. Uhlmann, both of Midland, Mich." should read
-- Gary N. Bokerman, Madison, Ind.; James E. Hampton, Midland, Mich. --.

Signed and Sealed this

Twentieth Day of October, 1992

Attest:

DOUGLAS B. COMER

*Attesting Officer*   *Acting Commissioner of Patents and Trademarks*